United States Patent
Taico et al.

(10) Patent No.: US 12,343,599 B1
(45) Date of Patent: Jul. 1, 2025

(54) FANATIC PARTICIPATION DEVICE

(71) Applicants: Daniel Freddy Chirinos Taico, Boca Raton, FL (US); Jorge Gabriel Luyo Pineda, Boca Raton, FL (US)

(72) Inventors: Daniel Freddy Chirinos Taico, Boca Raton, FL (US); Jorge Gabriel Luyo Pineda, Boca Raton, FL (US)

(*) Notice: Subject to any disclaimer, the term of this patent is extended or adjusted under 35 U.S.C. 154(b) by 0 days.

(21) Appl. No.: 19/083,159

(22) Filed: Mar. 18, 2025

(51) Int. Cl.
| *A63B 41/12* | (2006.01) |
| *A61B 5/08* | (2006.01) |
| *A61B 5/087* | (2006.01) |
| *A63F 9/00* | (2006.01) |
| *A63F 9/24* | (2006.01) |
| *G07F 17/32* | (2006.01) |

(52) U.S. Cl.
CPC .............. *A63B 41/12* (2013.01); *A61B 5/08* (2013.01); *A61B 5/087* (2013.01); *A63F 9/0079* (2013.01); *G07F 17/32* (2013.01); *G07F 17/3204* (2013.01); *G07F 17/3297* (2013.01); *A63F 2009/0083* (2013.01); *A63F 2009/0084* (2013.01); *A63F 2009/009* (2013.01); *A63F 2009/2442* (2013.01)

(58) Field of Classification Search
CPC ........... A63B 41/12; A61B 5/08; A61B 5/087; A63F 9/0079; A63F 2009/0083; A63F 2009/0084; A63F 2009/009; A63F 2009/2442; G07F 17/32; G07F 17/3204; G07F 17/3297

See application file for complete search history.

(56) References Cited

U.S. PATENT DOCUMENTS

| 1,368,115 | A | * | 2/1921 | Chester | ................. | A63F 9/0079 273/445 |
| 2,342,411 | A | * | 2/1944 | Lissiansky | ............. | G11B 17/00 369/191.1 |
| 4,425,797 | A | * | 1/1984 | Morrison | ............. | A63B 21/154 482/44 |
| 5,336,839 | A | * | 8/1994 | Haehn | .................... | B01D 53/18 95/155 |
| 6,030,350 | A | * | 2/2000 | Jiang | .................... | A61B 5/4082 600/23 |
| 7,134,665 | B2 | * | 11/2006 | Holsten | .................... | A63F 9/00 273/458 |

(Continued)

*Primary Examiner* — Peter J Bertheaud
(74) *Attorney, Agent, or Firm* — Ruben Alcoba, Esq.

(57) ABSTRACT

A fanatic participation device designed to enhance fan engagement at sporting events by transforming vocal enthusiasm into a tangible action—ball inflation. The device comprises a rectangular upright housing equipped with an air-compressor, weight and height sensors, a microphone, and a controller. Fans can inflate balls by screaming into the microphone, with inflation proportional to the decibel level detected. The device captures and displays fan images on a digital viewer and can publish team-related announcements. It also includes a transceiver for connectivity with smart devices, allowing real-time image transmission. Stability is ensured through a mechanical ball holder stabilizer and gusset plates. The balls inflated are ideally intended for use during fan teams' games, enabling direct participation. The device combines real-time feedback, interactivity, and promotional capabilities to create a memorable and immersive fan experience.

3 Claims, 7 Drawing Sheets

(56) References Cited

U.S. PATENT DOCUMENTS

| | | | | |
|---|---|---|---|---|
| 7,487,972 | B2* | 2/2009 | Halliburton | A63F 7/027 |
| | | | | 273/458 |
| 8,714,555 | B1* | 5/2014 | Kelsey | A63F 9/0079 |
| | | | | 273/458 |
| 8,967,625 | B2* | 3/2015 | Wang | G07F 17/38 |
| | | | | 273/440 |
| 10,453,313 | B2* | 10/2019 | Halliburton | A63F 9/0243 |
| 12,028,640 | B2* | 7/2024 | Bollman | H04N 9/8211 |
| 2015/0235524 | A1* | 8/2015 | Hedley | G07F 17/3297 |
| | | | | 273/451 |

\* cited by examiner

FANATIC PARTICIPATION DEVICE

BACKGROUND

Sporting events, particularly those involving ball sports such as soccer, basketball, handball, volleyball, and American football, have long been venues for fans to express their passion and enthusiasm for their favorite teams. The fervor of these fanatics is often shown through loud cheers, chants, and the use of various participation devices that amplify the experience of being part of the crowd. Enhancing fan engagement not only contributes to the atmosphere of the event but also strengthens the connection between fans and their teams. Traditional methods of fan participation, such as clapping, chanting, and waving flags, while effective, lack an interactive and measurable component that can directly reflect fan enthusiasm in a tangible way.

In recent years, there has been an increased interest in integrating technology into sports venues to create more interactive and immersive experiences for fans. Devices that respond to fan input, such as sound levels, offer a unique way to bridge the gap between fan energy and in-game elements. Additionally, the ability to capture, display, and transmit images of fans adds a layer of engagement that connects fans both within and outside the stadium.

The present invention addresses this need by introducing a fanatic participation device designed to amplify and materialize fan enthusiasm in real-time. The device is intended to be placed in stadiums, fan zones, and other venues where sports fanatics gather. By allowing fans to inflate a ball attached to the device based on the volume of their screams, this invention not only engages fans actively but also provides a visual representation of their passion. More importantly, the balls inflated by the device can be used in various ways, including during official games, fan activities, and even training sessions. This flexibility enables sponsors, teams, and venues to extend the interactive experience beyond match days, as the device can also be installed in sponsor stores weeks before games to inflate balls for team training sessions.

The incorporation of a digital viewer to display images of fans and a transceiver to transmit these images to other devices adds to the interactive appeal of the device. The device's ability to inflate a ball proportionally to the decibels of fan screams introduces a gamified element to the fan experience. Fans can visually see the impact of their enthusiasm, which enhances the excitement and involvement during events. The inclusion of a digital image recorder allows for capturing memorable moments of fan participation, which can be displayed on the digital viewer and shared with a wider audience. Additionally, the ability to publish announcements related to the teams on the digital viewer serves both an informative and promotional function, further enhancing the in-stadium and pre-game experience.

By integrating components such as weight sensors, height sensors, and mechanical stabilizers, the present invention ensures precision and stability in its operation. The use of a controller to manage these components efficiently guarantees a seamless and interactive experience for the fans. The capability to connect to a central hub or other smart devices through a transceiver allows for synchronized announcements and displays across multiple devices, making it a versatile solution for modern sports venues and commercial sports environments.

In summary, the fanatic participation device offers a novel approach to fan engagement by transforming vocal enthusiasm into a tangible action—ball inflation—while simultaneously capturing and displaying the fans' excitement. By allowing the inflated balls to be used during games, training sessions, and promotional events, the device extends its utility beyond match-day experiences. This combination of interactivity, real-time feedback, and connectivity addresses the growing demand for immersive fan experiences at sporting events while also serving as a practical tool for teams and sponsors in their promotional and training efforts.

SUMMARY

An object of the present invention is to provide a fanatic participation device that will enhance fan engagement at sporting events, particularly soccer matches, by transforming vocal enthusiasm into a tangible action—ball inflation. The fanatic participation device comprises a rectangular upright housing with a bottom side, a top side, a front wall, a rear wall, a left wall, and a right wall. An air-compressor is attached to a section of the bottom side, while a weight sensor is positioned on a second section of the bottom side.

A linear actuator attached to a front corner section of the bottom side supports a horizontal microphone adjustor, which in turn holds a microphone. The front wall of the housing defines a central vertical linear aperture, and a height sensor is attached to an outer front top section of the housing. The device also includes a manual swivel actuator, which rotates from an upright vertical position to a forty-five-degree angle toward the rear wall. Attached to this actuator is a ball holder, which secures a ball inflating needle connected to the air-compressor via a hose.

An object of the present invention is to provide a fanatic participation device that allows fans to inflate balls based on the decibel levels of their screams, with the inflated balls ideally intended for use during fan teams' games. The device captures fan screams through the microphone, and the controller, operatively connected to the linear actuator, air-compressor, and other components, processes the sound levels to control ball inflation proportionally.

The fanatic participation device further includes left and right volume unit meters attached to respective sections of the rear wall to display the volume of fan screams. A gusset plate with a central circular aperture is positioned at the corners of the housing to enhance stability. A mechanical ball holder stabilizer mounted to the bottom side of the gusset plate employs a rotary motor connected to left and right spindles, each holding trays that stabilize the ball holder when the manual swivel actuator is in the upright position.

Additionally, the device is equipped with a digital viewer mounted on an upper section of the rear wall to display images of fans captured by a digital image recorder. An object of the present invention is to provide a fanatic participation device that captures and displays images of fanatics screaming into the device, thereby enhancing the interactive experience. The controller, which is operatively connected to the digital viewer, digital image recorder, microphone, and other components, manages the display of fan images and announcements corresponding to the teams.

The device also includes a transceiver that allows the controller to connect to a central hub or other smart devices, enabling the transmission of fan images and real-time updates to multiple platforms. An object of the present invention is to provide a fanatic participation device that can publish announcements on the digital viewer related to the teams in which the fanatics participate.

In essence, the fanatic participation device offers a comprehensive solution for increasing fan participation and excitement at sports venues by combining real-time sound-based interactions, image capture and display capabilities, and seamless connectivity with other devices and platforms.

BRIEF DESCRIPTION OF THE DRAWINGS

These and other features, aspects, and advantages of the present invention will become better understood with regards to the following description, appended claims, and drawings where:

DESCRIPTION

Figure 1:
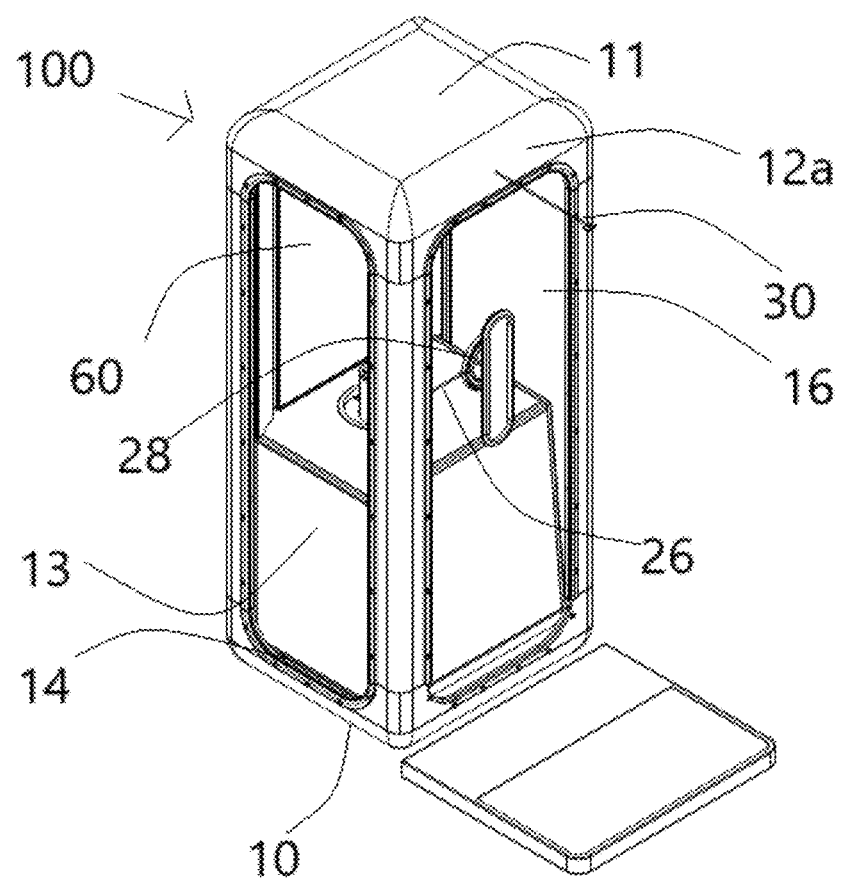
FIG. 1 is a left perspective view of the present invention.
Figure 2:
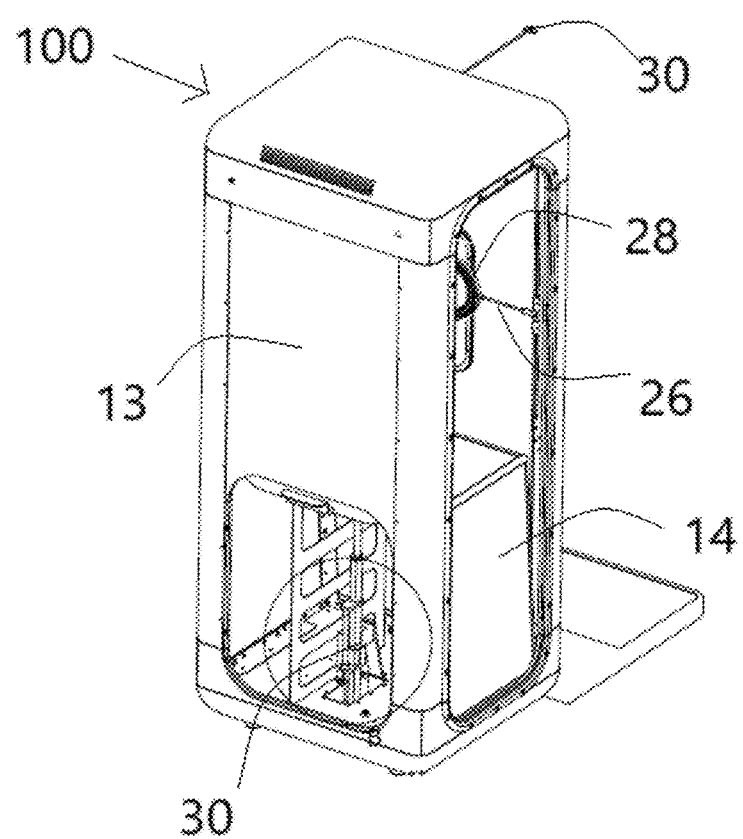
FIG. 2. is rear perspective view of the present invention.
Figure 3:
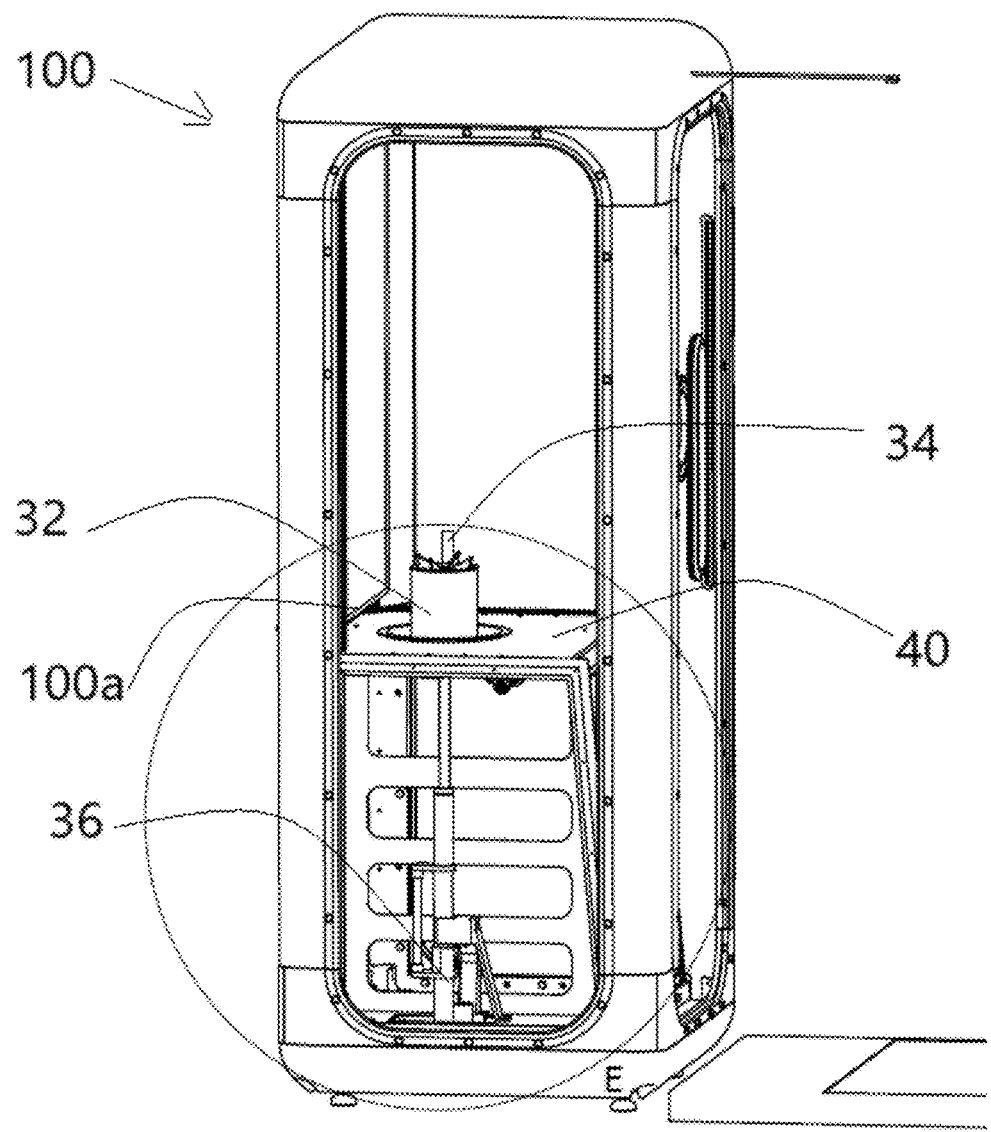
FIG. 3 is a left side view of the present invention.
Figure 4:
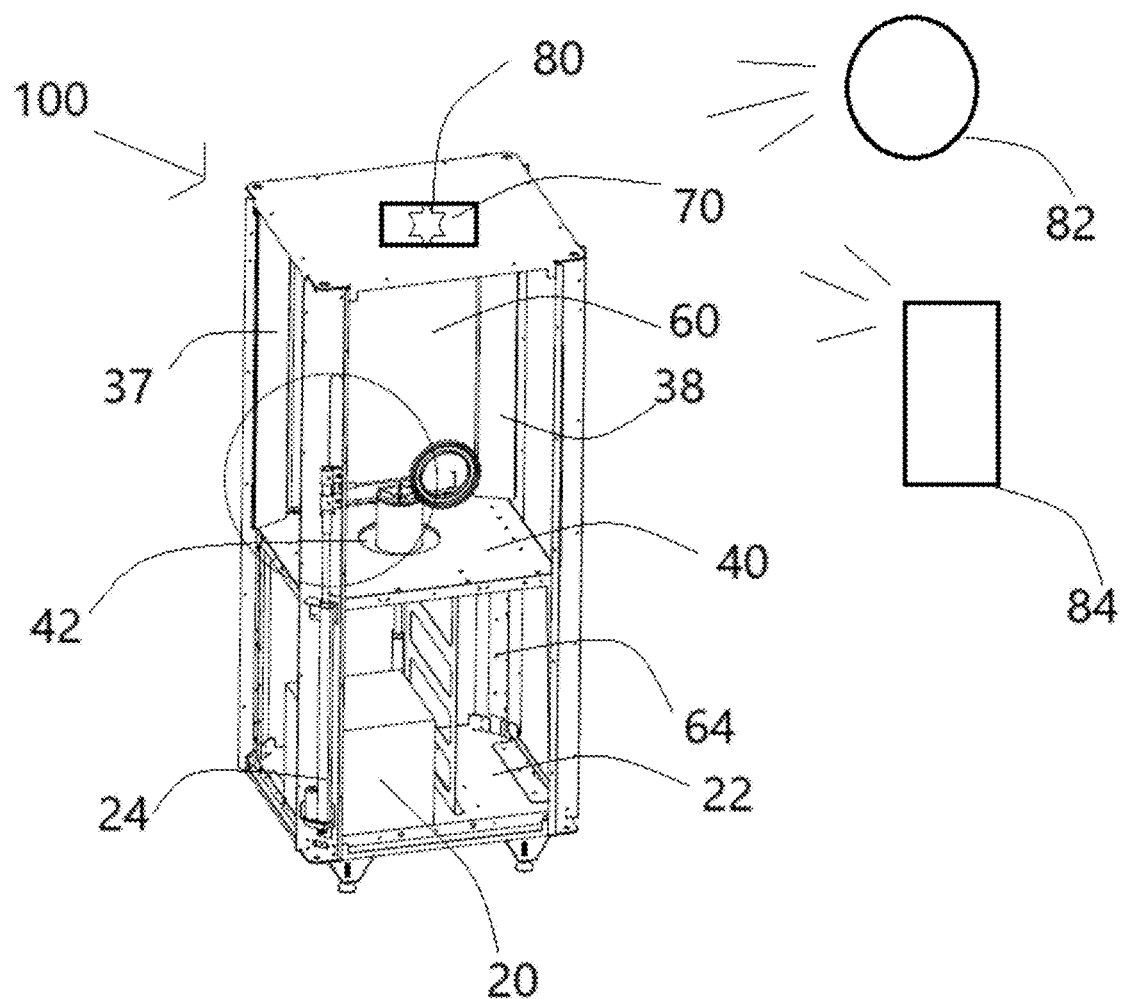
FIG. 4 is a front perspective view of the present invention.
Figure 5:
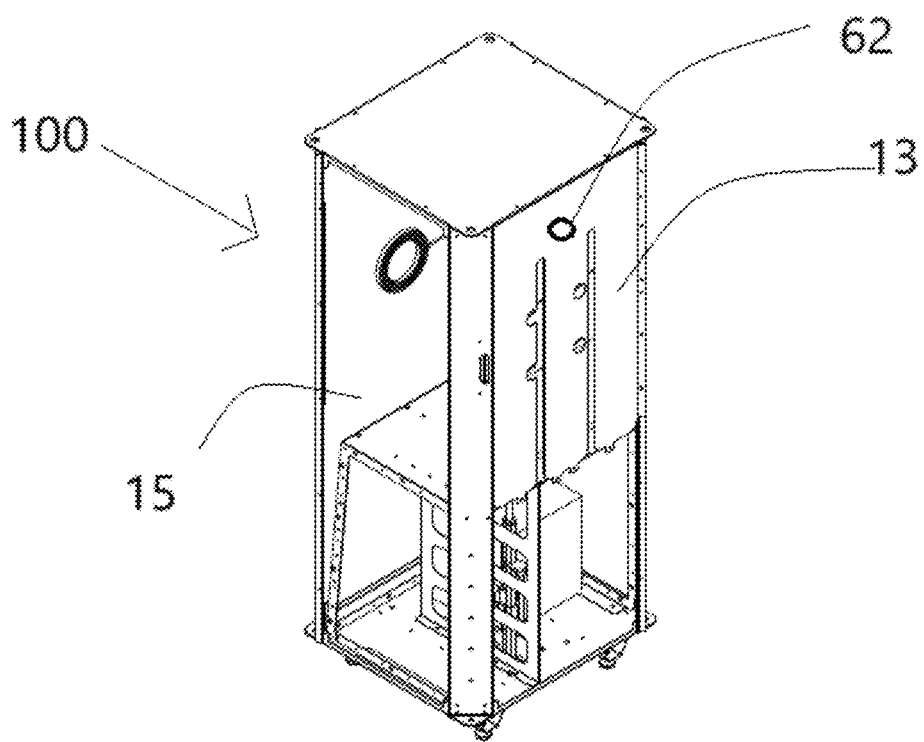
FIG. 5 is another rear perspective view of the present invention.
Figure 6:
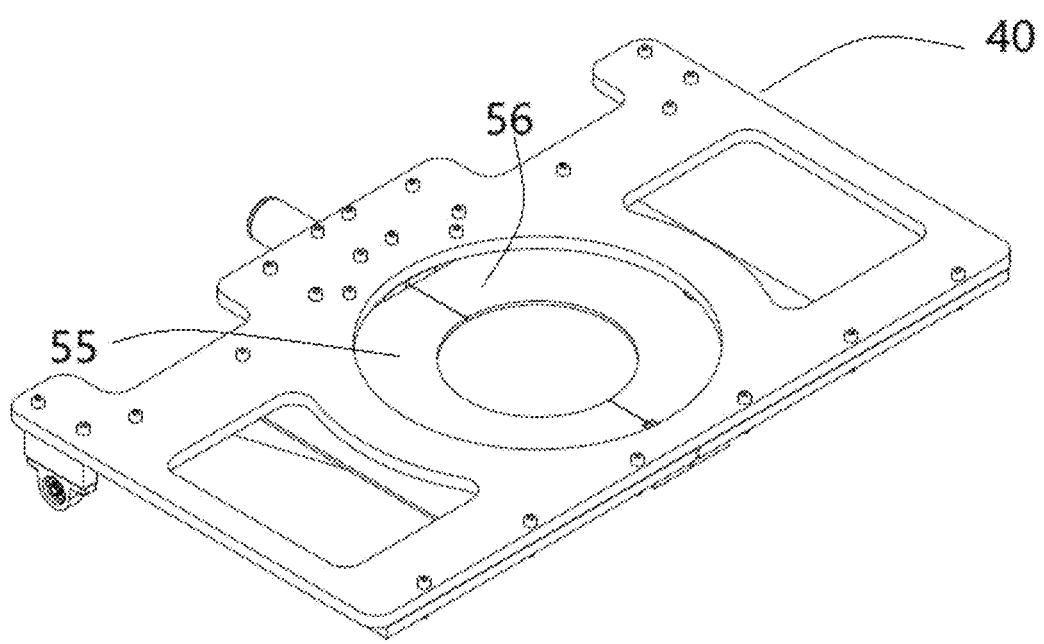
FIG. 6 is a perspective view of the gusset plate of the present invention.
Figure 7:
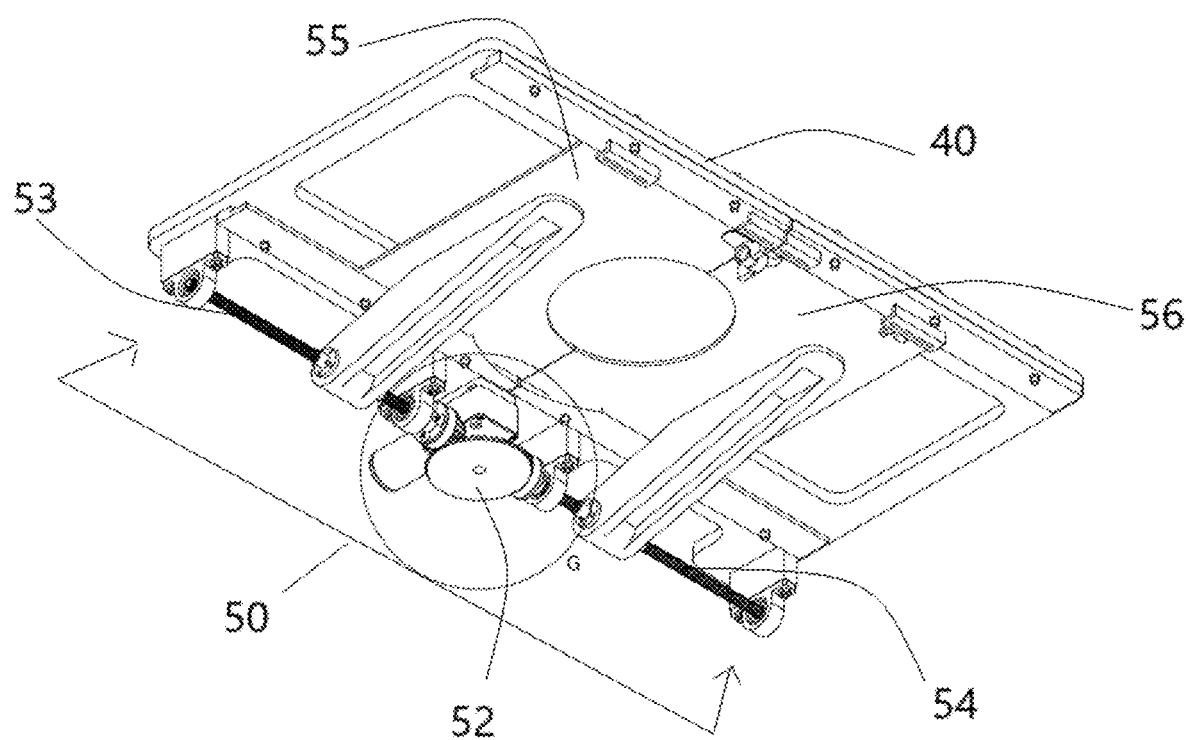
FIG. 7 is a bottom perspective view that shows how the mechanical ball holder stabilizer attaches to the bottom side of the gusset plate.

As seen in FIGS. 1-7, the present invention is a fanatic participation device.

The fanatic participation device comprises a rectangular upright housing 100 that has a bottom side 10, a top side 11, a front wall 12, a rear wall 13, a left wall 14 and a right wall 15. An air-compressor 20 is attached to a section of the bottom side 10. A weight sensor 22 is attached to a second section of the bottom side 10. A linear actuator 24 is attached to a front corner section of the bottom side 10, a horizontal microphone adjustor 26 is mounted on the linear actuator 24, and a microphone 28 is mounted on the horizontal microphone adjustor 26, the front wall 12 of the rectangular upright housing defines a central vertical linear aperture 16. A height sensor 30 is attached to an outer front top section 12*a* of the rectangular upright housing 100. A manual swivel actuator 30 is attached to a third section of the bottom side 10, the manual swivel actuator 30 rotates from an upright vertical position to a forty-five degree position that rotates toward the rear wall 13 of the rectangular upright housing 100. A ball holder 32 is attached to an upper section of the manual swivel actuator 30, a ball inflating needle 34 is secured to the ball holder 32. A hose 36 is positioned within the manual swivel actuator 30 and attaches to the ball inflating needle 34 and to the air-compressor 20. A left volume unit meter 37 is attached to a left section of the rear wall 13 and a right volume unit meter 38 is attached to a right section of the rear wall 13. A gusset plate 40 attaches to each corner of the rectangular upright housing 100 at a central position 100*a* of the rectangular upright housing 100, the gusset plate 40 defines a central circular aperture 42. A mechanical ball holder stabilizer 50 is mounted to a bottom side of the gusset plate 40, the mechanical ball holder stabilizer 50 uses a rotary motor 52 that attaches to a left spindle 53 and a right spindle 54, the left spindle 53 has a left tray 55 mounted on the left spindle 53 and the right spindle 54 has a right tray 56 that is mounted on the right spindle 54, the left tray 55 and the right tray 56 each define a half of an inward circle that allows the ball holder 32 to be stabilized within the mechanical ball holder stabilizer 50 when the manual swivel actuator 30 is in the upright vertical position. A digital viewer 60 that is mounted on an upper section of the rear wall 13. A digital image recorder 62 that is attached to an upper section of the rectangular upright housing 100. And, a controller 70 that is attached to the rectangular upright housing 100, the controller 70 is operatively connected to the linear actuator 24, to the air-compressor 20, to the digital viewer 60, to the microphone 28, to the mechanical ball holder stabilizer 50, to the weight sensor 22, to the digital image recorder 62, to the left volume unit meter 37 and to the right volume unit meter 38, and to the height sensor 30.

In an embodiment of the present invention, the controller 70 has a transceiver 80 that connects to a central wireless communication hub 82 or a smart device 84. A smart device is define to be A "smart device" is an electronic device that is connected to the internet, allowing it to collect, process, and transmit data, often with the ability to operate autonomously or interact with its environment through sensors and software, making it more than just a basic appliance; an example is a smartphone. A central wireless communication hub 82 is a device that acts as a central point for wireless devices to connect to a network, enabling them to communicate wirelessly. The smart device 82 can be used to communicate with the present invention remotely to allow a remote user to inflate any ball that is connected to the present invention.

In another embodiment of the present invention, the digital viewer 60 connects to a speaker system 64. In some embodiments the digital image recorder 62 is a camera.

The present invention offers several significant advantages that enhance the fan experience at sporting events, particularly in soccer stadiums:

Enhanced Fan Engagement: One of the primary advantages of the present invention is its ability to transform fan enthusiasm into a tangible action—ball inflation. By allowing fans to inflate balls based on the decibel levels of their screams, the device creates an interactive experience that encourages more active participation and makes fans feel directly involved in the event;

Direct Participation in Games: The balls inflated by the device are ideally intended to be used during fan teams' games. This feature allows fans not only to contribute their energy vocally but also to see their efforts manifest in a practical and visible way during the game, enhancing their sense of contribution and connection to the team;

Real-Time Feedback and Gamification: The integration of left and right volume unit meters provides real-time feedback to fans, displaying the volume of their screams instantly. This gamified element motivates fans to cheer louder and fosters a competitive and lively atmosphere within the stadium;

Image Capture and Display: The inclusion of a digital image recorder and a digital viewer enables the device to capture and display images of fans while they are participating. This feature adds a layer of excitement and recognition for fans, making their experience memorable and shareable;

Increased Connectivity and Information Sharing: The transceiver within the controller allows the device to connect to a central hub or other smart devices, facilitating the transmission of images and announcements. This capability enhances the stadium's ability to communicate with fans, deliver team-related announcements, and synchronize information across multiple displays;

Promotional and Marketing Opportunities: By displaying team-related announcements and capturing fan participation, the device offers a platform for promotional content. Teams and sponsors can leverage this feature to deliver targeted messages and enhance their branding during events;

Stability and Precision: The design of the device, including the mechanical ball holder stabilizer and gusset plates, ensures that ball inflation is stable and precise. This reduces the risk of malfunction and provides a smooth and reliable experience for fans;

Safety and User-Friendliness: The device's construction with weight and height sensors ensures it can accommodate fans of different statures safely. The manual swivel actuator and secure ball holder also simplify the inflation process, making it user-friendly for a wide range of participants;

Memorable and Immersive Experience: By combining vocal input, visual feedback, and connectivity, the present invention creates an immersive fan experience that goes beyond traditional cheering. This helps in building a stronger emotional connection between fans and their teams, making the event more memorable; and Innovative Use of Technology: The present invention integrates sound sensors, actuators, digital displays, and network connectivity in a novel manner. This combination of technologies not only enhances fan interaction but also sets a new standard for fan participation devices in sports venues. The present invention creates a new opportunity for fan interaction and branding by using one of the most iconic elements of a sporting event, the ball that is used during the event.

Overall, the present invention provides a comprehensive and innovative solution for boosting fan participation, enhancing the atmosphere at sporting events, and creating new opportunities for team branding and engagement.

The embodiments of the fanatic participation device herein are exemplary and numerous modifications, combinations, variations, and rearrangements can be readily envisioned to achieve an equivalent result, all of which are intended to be embraced within the scope of the appended claims. Further, nothing in the above-provided discussions of the fanatic participation device should be construed as limiting the invention to an embodiment or a combination of embodiments. The scope of the invention is defined by the description, drawings, and claims.

What is claimed is:

1. A fanatic participation device, the fanatic participation device comprises:
   a rectangular upright housing that has a bottom side, a top side, a front wall, a rear wall, a left wall and a right wall:
   an air-compressor is attached to a section of the bottom side;
   a weight sensor is attached to a second section of the bottom side;
   a linear actuator is attached to a front corner section of the bottom side, a horizontal microphone adjustor is mounted on the linear actuator, and a microphone is mounted on the horizontal microphone adjustor, the front wall of the rectangular upright housing defines a central vertical linear aperture;
   a height sensor is attached to an outer front top section of the rectangular upright housing;
   a manual swivel actuator is attached to a third section of the bottom side, the swivel actuator rotates from an upright vertical position to a forty-five degree position that rotates toward the rear wall of the rectangular upright housing,
   a ball holder is attached to an upper section of the manual swivel actuator, a ball inflating needle is secured to the ball holder;
   a hose is positioned within the manual swivel actuator and attaches to the ball inflating needle and to the air-compressor;
   a left volume unit meter is attached to a left section of the rear wall and a right volume unit meter is attached to a right section of the rear wall;
   a gusset plate attaches to each corner of the rectangular upright housing at a central position of the rectangular upright housing, the gusset plate defines a central circular aperture;
   a mechanical ball holder stabilizer is mounted to a bottom side of the gusset plate, the mechanical ball holder stabilizer uses a rotary motor that attaches to a left spindle and a right spindle, the left spindle has a left tray mounted on the left spindle and the right spindle has a right tray that is mounted on the right spindle, the left tray and the right tray each define a half of an inward circle that allows the ball holder to be stabilized within the mechanical ball holder stabilizer when the manual swivel actuator is in the upright vertical position;
   a digital viewer that is mounted on an upper section of the rear wall;
   a digital image recorder that is attached to an upper section of the rectangular upright housing; and
   a controller that is attached to the rectangular upright housing, the controller is operatively connected to the linear actuator, to the air-compressor, to the digital viewer, to the microphone, to the mechanical ball holder stabilizer, to the weight sensor, to the digital image recorder, to the left volume unit meter and to the right volume unit meter, and to the height sensor.

2. The fanatic participation device of claim 1, wherein the controller has a transceiver that connects to either a central wireless communication hub or a smart device.

3. The fanatic participation device of claim 2, wherein the digital viewer connects to a speaker system.

* * * * *